United States Patent
Vancaillie et al.

(10) Patent No.: US 7,473,246 B2
(45) Date of Patent: Jan. 6, 2009

(54) MEDICANT RECONSTITUTION CONTAINER AND SYSTEM

(75) Inventors: Joost M. Vancaillie, Lombise (BE); Georges Rondeau, Braffe (BE); Eric Tomasetti, Jemeppe/s/Sambre (BE)

(73) Assignees: Baxter International Inc., Deerfield, IL (US); Baxter Healthcare S.A., Wallisellen, Zurich (CH)

( * ) Notice: Subject to any disclaimer, the term of this patent is extended or adjusted under 35 U.S.C. 154(b) by 58 days.

(21) Appl. No.: 11/425,815

(22) Filed: Jun. 22, 2006

(65) Prior Publication Data

US 2007/0299419 A1 Dec. 27, 2007

(51) Int. Cl.
A61M 5/32 (2006.01)
A61B 19/00 (2006.01)
B65B 1/04 (2006.01)
B65B 3/04 (2006.01)
B67C 3/00 (2006.01)

(52) U.S. Cl. .................. 604/411; 604/403; 604/408; 604/409; 604/415; 604/416; 141/314; 141/329; 141/330; 141/363

(58) Field of Classification Search .............. 604/408, 604/410, 411, 412, 413, 414, 415, 416, 905, 604/43, 44, 181, 187, 188, 262, 272–274; 285/3, 260; 141/314, 329, 330, 363; 206/219, 206/222; 137/68.29, 68.3, 67
See application file for complete search history.

(56) References Cited

U.S. PATENT DOCUMENTS

| 4,392,850 A * | 7/1983 | Elias et al. ............... 604/82 |
|---|---|---|
| 4,410,321 A | 10/1983 | Pearson et al. |
| 4,411,662 A | 10/1983 | Pearson |
| 4,432,755 A | 2/1984 | Pearson |
| 4,534,758 A * | 8/1985 | Akers et al. ............... 604/85 |
| 4,583,971 A | 4/1986 | Bocquet et al. |
| 4,606,734 A | 8/1986 | Larkin et al. |
| 4,735,608 A * | 4/1988 | Sardam ............... 604/89 |
| 4,936,841 A | 6/1990 | Aoki et al. |
| 4,997,430 A * | 3/1991 | Van der Heiden et al. ... 604/414 |
| 5,304,163 A * | 4/1994 | Bonnici et al. ............... 604/403 |

(Continued)

FOREIGN PATENT DOCUMENTS

EP 0 091 310 A2 10/1983

(Continued)

*Primary Examiner*—Leslie Deak
*Assistant Examiner*—Adam Marcetich
(74) *Attorney, Agent, or Firm*—Jeffrey C. Nichols; Joseph P. Reagen; Austin J. Foley (57) ABSTRACT

A medicant reconstitution system is provided which has a generally flexible fluid bag with associated administration and reconstitution ports. The reconstitution port is adapted for receiving a medicant container and the administration port is for administering a medical fluid to a patient. According to one aspect of the present invention, the administration and reconstitution ports are integrated in a relatively rigid port structure. According to another aspect of the present invention, the reconstitution port receives a piercing member which is rotatable to a selected position to establish fluid flow. According to yet another aspect of the present invention, one of the reconstitution port and the piercing member includes a cutting edge, while the other includes a frangible member. Contact between the cutting edge and the frangible member opens the frangible member to establish fluid flow.

18 Claims, 10 Drawing Sheets

U.S. PATENT DOCUMENTS

| | | | |
|---|---|---|---|
| 5,308,347 A | 5/1994 | Sunago et al. | |
| 5,352,191 A | 10/1994 | Sunago et al. | |
| 5,364,386 A | 11/1994 | Fukuoka et al. | |
| 5,769,086 A * | 6/1998 | Ritchart et al. | 600/566 |
| 5,826,713 A | 10/1998 | Sunago et al. | |
| 6,159,192 A | 12/2000 | Fowles et al. | |
| 6,179,822 B1 * | 1/2001 | Niedospial, Jr. | 604/408 |
| 6,394,993 B1 * | 5/2002 | Chang et al. | 604/415 |
| 2005/0098209 A1 * | 5/2005 | Mackal | 137/68.3 |
| 2006/0025747 A1 * | 2/2006 | Sullivan et al. | 604/411 |

FOREIGN PATENT DOCUMENTS

| | | |
|---|---|---|
| EP | 0 091 311 B1 | 1/1988 |
| EP | 0 172 836 B1 | 5/1989 |
| EP | 0 416 454 A2 | 3/1991 |
| EP | 0 335 378 B1 | 10/1993 |
| WO | 86/01712 A1 | 3/1986 |
| WO | 03/082398 A2 | 10/2003 |
| WO | PCT/US2007/071743 | 11/2007 |

* cited by examiner

MEDICANT RECONSTITUTION CONTAINER AND SYSTEM

BACKGROUND OF THE INVENTION

1. Field of the Invention

This invention generally relates to systems for allowing selective fluid communication between fluid containers, such as medicant and/or medical fluid containers. More particularly, the invention relates to fluid containers of the type having a port adapted for receiving a medicant container for mixing with a fluid within the medical fluid container and an administration port for delivery of the combined medicant and fluid.

2. Description of Related Art

Medical solutions are provided in containers of several different constructions. For many years and even today solutions were provided in rigid containers such as glass containers. Other containers are not rigid but exhibit varying degrees of flexibility. These containers include blow molded containers which may be constructed of plastics including high density polyethylene. Containers made out of films form another type of flexible or non-rigid containers. Such containers or bags are typically formed of two flexible sheets or films of material joined at their peripheral edges by well-known methods, such as sonic, heat, or RF sealing.

Containers for medical solutions may contain one or more ports to allow the administration of a preferred solution to a patient. For example, the container may include a separate injection and administration port. The injection port allows a fluid to be added to the contents of the container while maintaining the sterility of the container. The administration port allows connection of the contents of the container to an administration set so that the contents may be provided to a patient.

In flexible containers, the containers include separate fill and administration ports which extend through a wall or seam of the bag. More specifically, such ports typically include plastic tubular members bonded within the peripheral seal, which allow for communication between an interior of the bag and the exterior. The tubular members are temporarily sealed by any of a number of conventional sealing devices, such as a pierceable diaphragm or frangible cannula, which are also all well known to those skilled in the medical fluid container field.

As noted above it is often necessary to mix a medication with the contents of a medical fluid container to dilute or reconstitute a medicament for administration to a patient. These medications are frequently provided in a glass vial closed by a pierceable rubber stopper or septum. From time to time herein, the terms "vial," "vial connection port," and other uses of the word "vial" will be used in reference to a medical container, but it should be understood that the present invention is not limited to use with a glass vial, but can be applied to any medicant container which includes a connection system which allows access to the contents of the container for reconstitution and/or withdrawal. Also, as used herein "reconstitution" or "reconstituting" includes reconstitution or reconstituting a dry or powder medicant, dilution or diluting a medicant, either powder or liquid, and other mixing of medicants in the vial and/or container.

If the medicant in the vial is provided as a fluid it may be withdrawn from the vial and added directly to the medical fluid container for administration to a patient. In other situations where the medicant is lyophilized, liquid is first introduced into the vial to reconstitute the medicament, and then the reconstituted medicament is withdrawn from the vial and injected into the container. In some examples liquid used to reconstitute the medicant may be withdrawn from the solution container. One way to accomplish this is to form a direct connection between the vial and the container. In this regard it was previously known to provide a port on the top end edge of a medical fluid container for engaging and supporting the separate medicament container.

In such known containers with a vial connection port at the top, it is known to employ a piercing member axially movable within the port to pierce the septum of the vial to provide access to the contents. Alternatively, the piercing member may be stationary, while the vial is movable relative to the piercing member. The piercing member may also include a lumen through which a medicant and/or medical fluid may pass between the interior of the bag and the vial.

When the vial medicant enters the interior of the bag, it mixes with a fluid already contained within the bag ("the bag medicant"). The vial medicant and bag medicant are mixed until they form a treatment fluid. The administration port at the bottom end of the bag is then opened and the treatment fluid is delivered to a patient through a separate administration tubing set connected to the administration port.

Variations of the above-described reconstitution system are illustrated in U.S. Pat. No. 4,410,321; 4,411,662; 4,432,755; 4,583,971; 4,606,734; 4,936,841; 5,308,347; 5,352,191; 5,364,386; and 5,826,713; each being hereby incorporated herein by reference.

Heretofore, the vial connection port and administration ports of the above containers have typically been provided at opposite ends of the bag in order to allow for the contents of the vial to utilize gravity to flow from the vial, through an upper inlet or connection port, and into the bag interior, then out of the bag through a lower administration port. This configuration, however, requires multiple openings at opposite ends of the peripheral seal of the bag, including at least one at the vial connection port and another at the administration port, which increases the cost and complexity of assembling the bag. Further a location for connection of the vial at the top of the bag can be awkward and inconvenient for hanging the bag. On the other hand, placing the vial connection at the bottom of the container may cause fluid to drain and remain in the vial and not be administered to the patient.

Also, with known containers used for reconstituting medications in vials, the associated piercing member for accessing the vial contents typically has an open lumen, which provides continuous fluid communication between the vial and the container interior immediately after the vial stopper has been pierced. Known reconstitution containers generally do not allow for interruption or control of fluid flow between the vial and container after fluid communication is established, and therefore require that the vial and container remain attached to avoid leakage or contamination. This does not allow for accessing multiple vials should the prescription call for such concentrations.

As set forth in more detail below, the present invention provides an improved container and container system for medicant reconstitution that have several aspects that may be employed separately or together to address one or more of the above drawbacks of prior containers and systems.

SUMMARY OF THE INVENTION

The present invention, in one aspect, provides a medicant reconstitution system that comprises a fluid container, such as an IV fluid container, for example, a bag that generally defines an interior chamber capable of containing a medical fluid, such as saline or other liquid. The bag generally includes a top end and a bottom end. In accordance with one aspect of the present invention, the bottom end of the bag is defined at least in part by a port structure. The port structure may preferably be more rigid than the bag and includes a reconstitution port adapted to receive a medicant container and an administration port for delivery of medical fluid, which ports are integrally formed as part of the port structure.

As noted above, when used herein, the term "reconstitution" is intended to refer generally to any use of a system according to the present invention for combining a medicant with a fluid. By way of example, the combination can be between a dehydrated or lyophylized medicant and a reconstituting fluid, between a concentrated liquid medicant and a diluent fluid, between two liquid medicants, etc. "Medicant" and "drug" are also used interchangeably herein and are intended to be broadly construed and include any substance or composition that may be administered to a patient for therapeutic or diagnostic purposes. Without limiting the foregoing, a medicant or drug may be liquid or powder, may be chemical, cellular, radiopaque, radioactive or have other properties or forms without departing from the present invention.

In accordance with another aspect of the present invention, a medicant reconstitution system is provided which comprises a generally flexible bag that defines an interior chamber capable of containing a medical fluid. The bag includes a top end and a bottom end. The bottom end of the bag includes an administration port for delivering medical fluid to a patient. A reconstitution port adapted to receive a medicant container is associated with the bag and has an opening into the interior chamber. A piercing member is received within the reconstitution port and includes a spike for piercing a membrane of a medicant container received by the reconstitution port. The piercing member also includes a rotatable barrel which forms a lumen communicating with an interior aperture of the piercing member. Fluid communication between the bag and an exterior aperture of the piercing member is provided by rotation of the barrel to a selected position.

In accordance with yet another aspect of the present invention, a medicant reconstitution system comprises a generally non-rigid or flexible container, for example a bag that defines an interior chamber capable of containing a medical fluid. The bag includes a top end and a bottom end. The bottom end of the bag includes an administration port for delivering medical fluid to a patient. A reconstitution port adapted to receive a medicant container is associated with the bag. A member is rotatably received within the reconstitution port and one of the reconstitution port and the member includes a cutting edge, while the other includes a frangible member, which is breakable by the cutting edge to define an opening therethrough. The member is rotatable with respect to the reconstitution port to bring the cutting edge and frangible member into contact to open the frangible member and allow fluid flow from the interior chamber of the bag, through a passageway formed by a piercing member and into a medicant container received by the reconstitution port.

DESCRIPTION OF THE PREFERRED EMBODIMENTS

Although the present invention is described as illustrated in the attached drawings of the preferred embodiment, it is to be understood that the disclosed embodiments are merely exemplary of the invention, which may be embodied in various forms. Therefore, specific details disclosed herein are not to be interpreted as limiting, but as a representative basis for teaching one skilled in the art to variously employ the present invention in virtually any appropriate manner.

Figure 1:
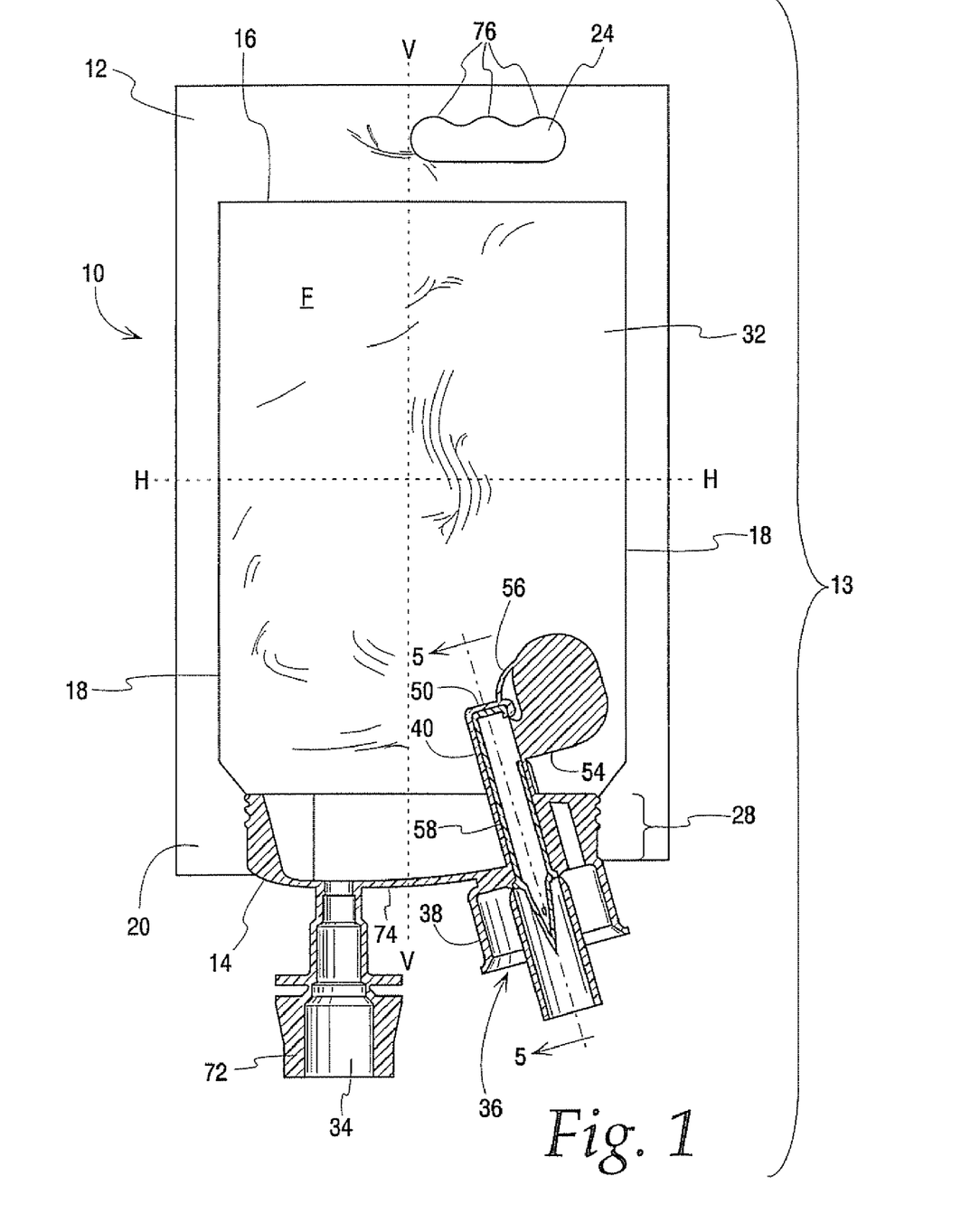
FIG. 1 is a front elevational view of one embodiment of a drug reconstitution container system according to an aspect of the present invention, having a port structure shown in sectional view.

FIG. 1 shows a drug reconstitution system 10 according to the present invention. The illustrated drug reconstitution system 10 has two primary components—a generally flexible IV bag portion 12 and a port structure portion 14, which together form the unitary container 13 for intravenous or other medical fluid. The flexible bag portion 12 may be formed by any of a number of methods, for example by joining two flexible sheets at a top end 16 and two side edges 18, leaving an opening at a bottom end 20. These three sealed edges 16 and 18, along with the bottom end 20, are collectively referred to herein as the peripheral edges of the flexible bag portion 12. The top end 16 includes a hanger aperture 24, which is preferably laterally offset from a central vertical axis V of the flexible bag portion 12, as shown in FIG. 1. Although typically formed of separate facing sheets, the flexible bag portion 12 could be formed of a single sheet of flexible material, folded and sealed to form the peripheral edges. Any other known method of IV bag manufacture, such as blow molding or vacuum forming, is acceptable as well.

Figure 2:
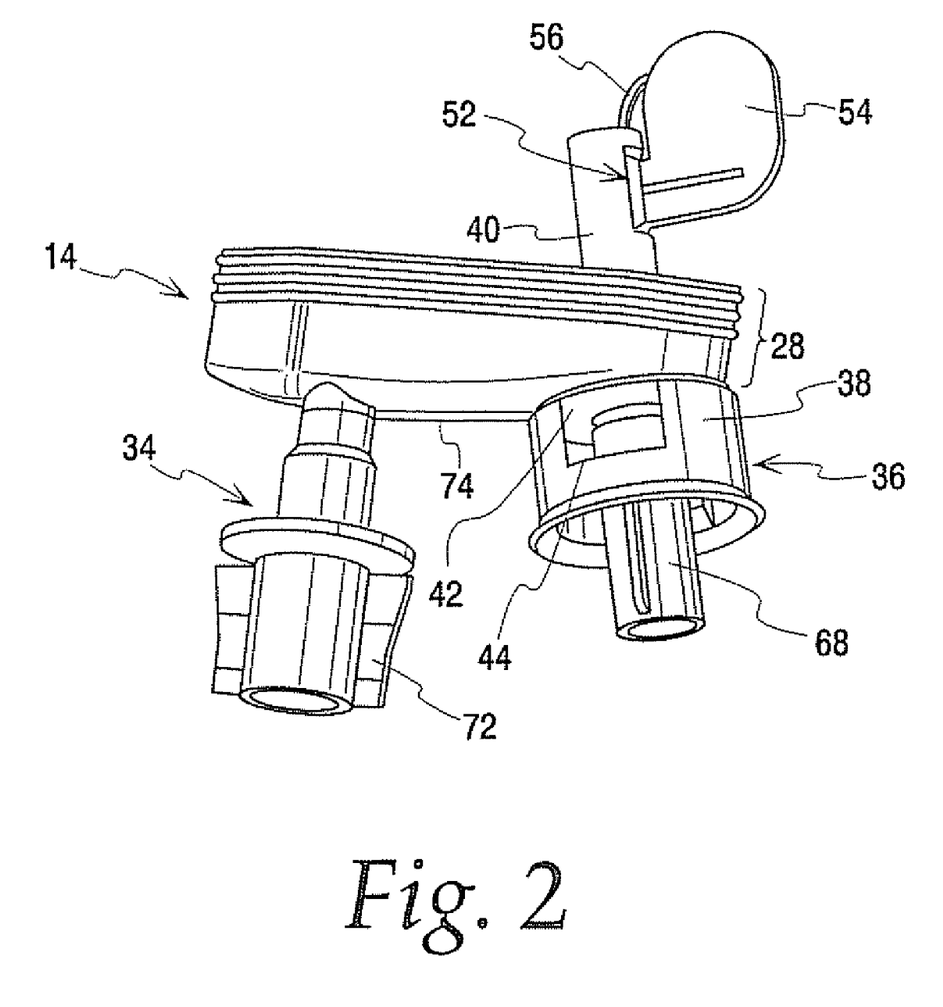
FIG. 2 is a front perspective view of the port structure of FIG. 1, isolated from the remainder of the drug reconstitution system.

The port structure 14, illustrated in detail in FIG. 2, is preferably sized and configured to fit within an opening (not illustrated) in the bottom end 20 of the IV bag 12. In a preferred embodiment, the opening and port structure 14 are substantially as wide as the top edge 16, so the port structure 14 essentially defines the entire bottom surface of the bag 12. The port structure 14 is formed of a plastic material that in the preferred embodiment is less flexible than the bag portion 12 and is preferably molded as essentially a single, integral unit. In this respect, the preferred port structure 14 may be considered as having intermediate rigidity, as it is preferably more rigid than the generally flexible bag 12, but less than completely rigid such as glass or metal. As will be seen from the description which follows, the port structure 14 has diverse aspects, such that certain portions may be more rigid and certain portions may be less rigid. While it has been found that high-density polyethylene may be provided in varying thicknesses to result in suitable rigidity of the port structure, it is contemplated that the port structure also may be fashioned from a combination of materials to provide differing characteristics at different locations.

In one manner of constructing the container 13, a portion of the port structure 14 is inserted through the opening in the bottom edge 20 of container or bag 12, such that the bottom edge 20 of the bag 12 overlies a seal area 28 of the port structure 14. The port structure 14 is bonded to the bottom edge 20 along the seal area 28 using known methods, such as heat sealing, radiofrequency, sonic or laser welding. When the bottom opening is sealed to the port structure 14, an open interior chamber 32 of the unitary container 13 is defined by the flexible bag portion 12 and port structure 14. The illustrated container 13 has a single chamber or compartment, but it is contemplated that the present invention also can be practiced with containers having a plurality of interior chambers or compartments.

In a preferred embodiment, the container 13 is created in an orientation whereby the port structure 14 forms a side of the container. In this embodiment, during manufacturing the two films are withdrawn from rolls, extended along the manufacturing line and juxtaposed in an adjacent relationship. A permanent seal is created along the bottom edge 18 by a heated bar that spans the width of the two overlapping films and sealingly attaches the two films to each other. A permanent seal is then created by a heated bar along one of the edges 16, forming a side, and the other side opening is sealed to the port structure 14 to form the sealed edge 20. The sealed lower and two side edges thus form an interior capable of holding a fluid F. The fluid F is then injected into this interior through the open top edge. After filling, the heated bar, which created the seal along the bottom edge, is used to seal the films together along the top edge 18. This seal also forms the bottom edge 18 of the container being manufactured immediately after the present container. A slicing cut is then applied to the film along this seal. The container 13 is formed, and the process of forming the side edges on the next container begins. The side edges 18 are sealed together to define a sidewall and the port structure 14 is sealed into the bottom opening (oriented in a sideways position), then the container 13 is filled through a top opening before the top edge 18 is sealed.

In other embodiments, the interior chamber 32 of the container 13 may be filled with a fluid F through a separate fill port, or through an administration port 34 of the port structure 14. The chamber may also be filled before the port structure is attached or via use of sacrificial ports.

In addition to the administration port 34, the preferred port structure 14 also includes a reconstitution port 36. The illustrated port structure 14 is an intermediate rigidity, integral unit which combines the administration and reconstitution ports 34 and 36 as a preformed molded unit that may be attached to the edge 20 in a single, efficient, high speed sealing procedure. An example of this sealing procedure being described above. As will be seen below, several aspects of the present invention may be practiced using two separate ports at the bottom end of the bag or even at different sides, but the illustrated embodiment is preferred because it reduces the total number of components used and simplifies the manufacturing process.

Figure 5:
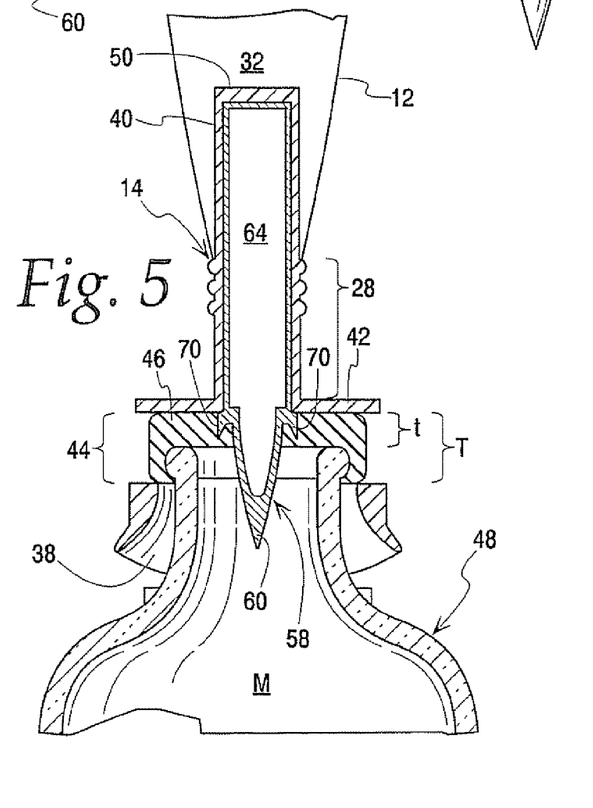
FIG. 5 is a side sectional view of a vial connected to the reconstitution port of FIG. 2, along the line 5-5 of FIG. 1.

The illustrated reconstitution port 36 has a vial docking arrangement that includes a docking sleeve 38 at a lower portion of the port structure 14 and an inlet chamber 40 at an upper portion, both integrally formed as part of the port structure 14. The vial docking sleeve 38 is a generally tubular, optionally tapered extension which is configured to receive the mouth of a vial or other medicant container. As shown in FIGS. 2 and 5, a circular upper wall 42 at a distal end of the docking sleeve 38 has a central aperture that opens into the inlet chamber 40.

In a preferred embodiment, illustrated in FIGS. 2 and 5, the docking sleeve 38 includes a plurality of stopper-retaining or end-retaining slots 44 adjacent to the upper wall 42. The slots or windows 44 are intended to receive the end of the vial 48 or the vial closure, which includes a pierceable membrane 46. As shown in FIG. 5, the diameter of the top of the vial or of the pierceable membrane or stopper 46 is slightly greater than a minimum diameter of the docking sleeve 38. The docking sleeve 38 is preferably comprised of a rigid, yet slightly resilient material, such that the end of the vial stretches the docking sleeve 38 outward as it is advanced toward the upper wall 42. After the end of the vial clears the end of the docking sleeve 38, it is located in the region of the slots 44 and the docking sleeve 38 returns to its unstretched diameter, locking behind the enlarged end of the vial, thereby preventing the vial 48 from being removed from the reconstitution port 36. The slots 44 may have a length substantially the same as the thickness T of the end of the vial to provide for a relatively tight fit.

Figure 9A:
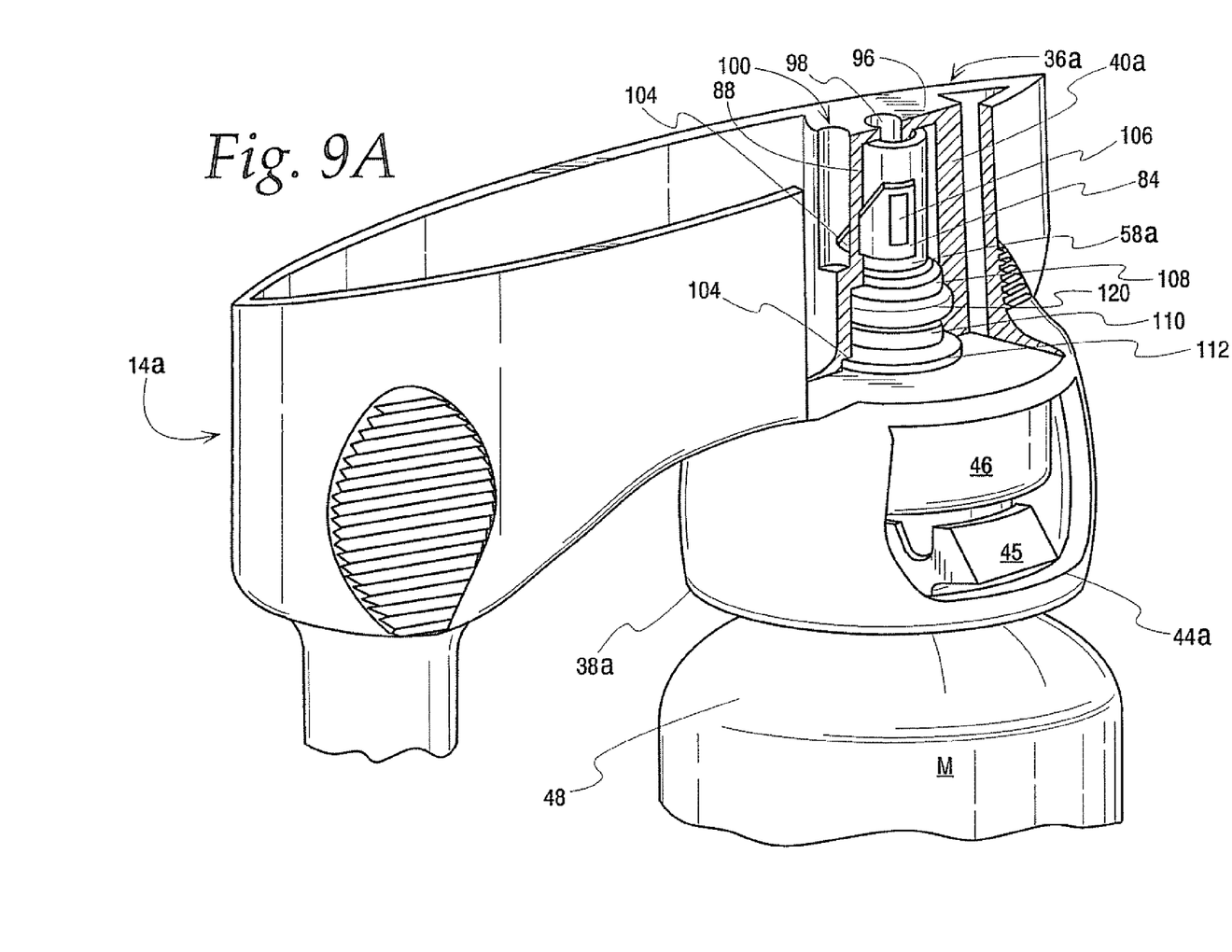
FIG. 9A is a front perspective view of the assembly of FIG. 8 in an intermediate position, with certain parts broken away for clarity.

In an alternative embodiment shown in FIG. 9, at least one slot 44a includes a resilient tab 45 which yields outwardly as medicant container 48 is inserted into docking sleeve 38a, which tab 45 thereafter returns to its original configuration to engage the underside of the top end of the vial or of pierceable membrane 46 and prevent removal of medicant container 48. In the illustrated embodiments of docking sleeve 38 in FIG. 5 and docking sleeve 38a in FIG. 9, the vial 48 cannot be readily removed, which makes the composition of any mixture within the bag 12 completely verifiable and traceable.

The inlet chamber 40 is preferably a hollow cylindrical extension of the reconstitution port 36, which projects into the interior chamber 32 of the bag 12. A lower end of the inlet chamber 40 opens into the docking sleeve 38, while an upper end is closed by an endcap 50. The inlet chamber 40 preferably includes a lateral window or opening 52, which can be seen in an open position in FIG. 4. The lateral window 52 is preferably closed by a frangible member 54 which is connected to the endcap 50 by a tether 56. To open the lateral window 52, a user grasps the frangible member 54 through the walls of the bag 12 and bends it to break a frangible connection at window 52, thereby opening the window 52. The tether 56 prevents the frangible member 54 from floating freely within the interior chamber 32 of the container 13 after it has been broken away from the chamber 40.

Figure 3:
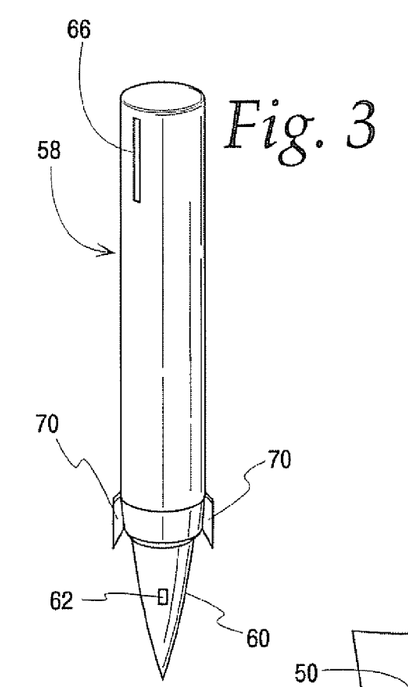
FIG. 3 is a front perspective view of one embodiment of the piercing member employed in the reconstitution port of FIG. 1.
Figure 3A:
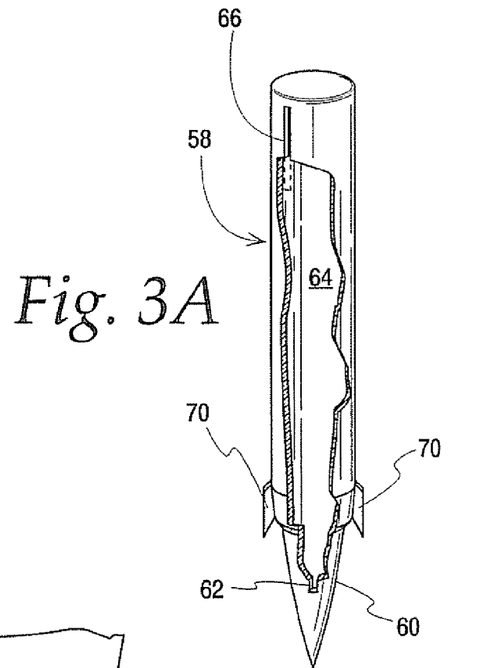
FIG. 3A is a front perspective view of the piercing member of FIG. 3, with selected portions broken away to show an inner lumen.

To access vial contents, a piercing member 58, as illustrated in FIGS. 3 and 3A, is provided within the reconstitution port 36. The piercing member 58 is preferably rotatable within the inlet chamber 40 of the reconstitution port 36. The piercing member 58 has a generally tubular body with a piercing point or spike 60 at a distal end. As illustrated in FIG. 5, the spike 60 is sufficiently sharp to pierce through the pierceable thickness "t" of a pierceable membrane 46 of a medicant container 48, such as the rubber stopper or septum of a vial. An exterior aperture 62 is located on the spike 60 at a location which will pass beyond the pierceable thickness t and enter the interior of the medicant container. The exterior aperture 62 opens into a lumen 64 within the piercing member 58. The lumen 64 extends between the exterior aperture 62 at a distal end of the piercing member 58 to an interior aperture 66 at an upper or proximal end of the piercing member 58.

The piercing member 58 is oriented within the inlet chamber 40, such that the spike 60 extends into the docking sleeve 38. As shown in FIG. 2, preferably, a removable spike protector 68 is located over the spike 60 in order to maintain the spike 60 in a sterile condition before use and to prevent a user from inadvertently contacting the spike 60. The spike protector may be molded as one piece with the port structure and have a thin breakable or frangible circumferential area to allow easy user removal for access to the spike. The protector 38 may be molded in the form of a tube and then the lower edge is pinched and heat sealed to provide a sterile barrier. Of course, the spike protector 68 can be located to cover the entire docking sleeve 38, in addition to the spike 60 itself.

Figure 4:
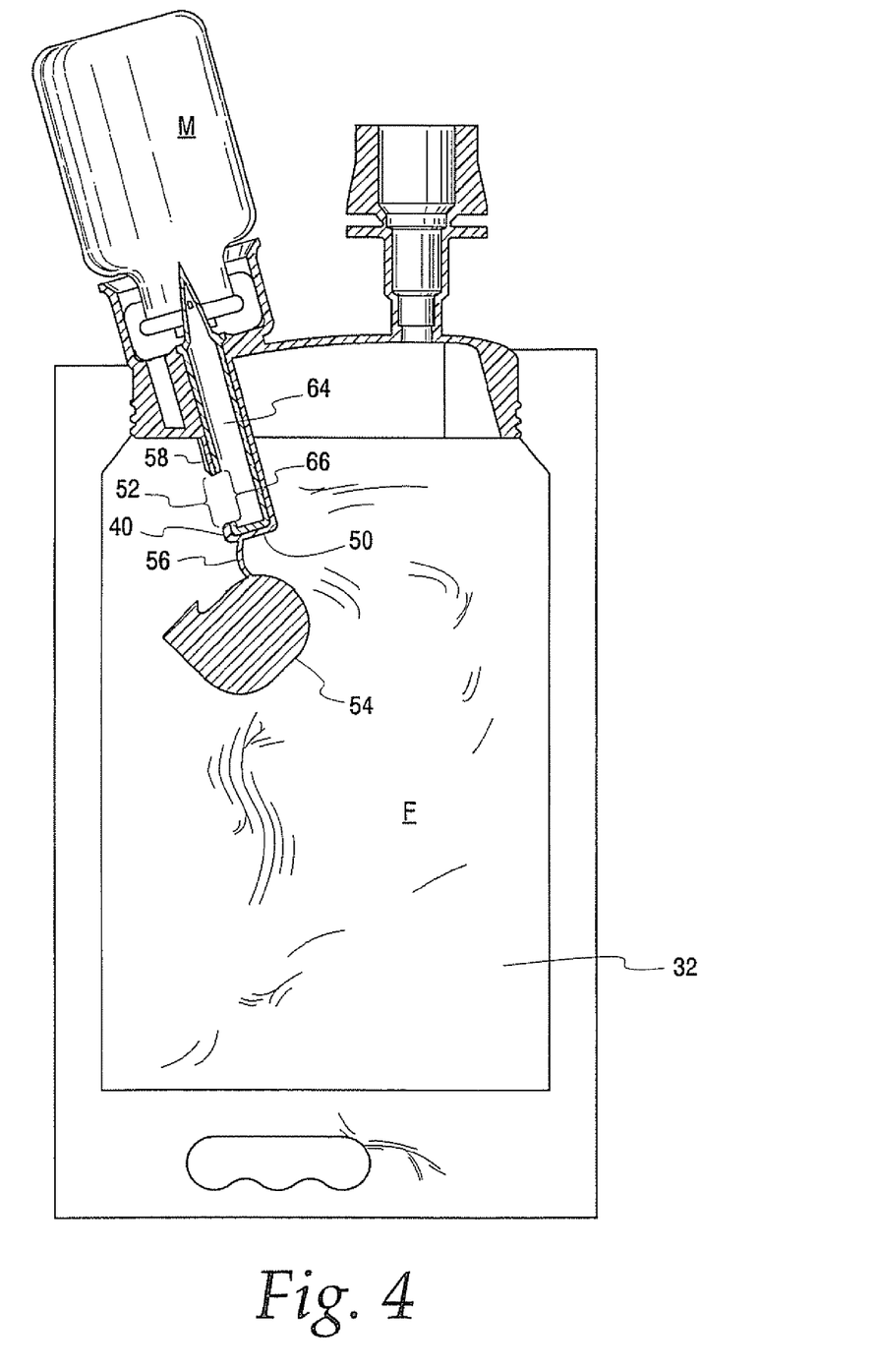
FIG. 4 is a front elevational view of the drug reconstitution system of FIG. 1, inverted during a mixing step.

It will be seen that the lumen 64 defines a flow path between the interior chamber 32 of the container 13 and the exterior aperture 62 when the interior aperture 66 is aligned with the lateral window 52, according to the orientation of FIG. 4. However, the frangible member 54 closes the lateral window 52 of the inlet chamber 40, thereby preventing the fluid F from escaping into the interior aperture 66, through the lumen 64, and out of the exterior aperture 62. In order to initially open the flow path, the frangible member 54 is broken away from the chamber 40, then the pierceable member 58 is rotated until the interior aperture 66 is in alignment with the chamber lateral window 52, as shown in FIG. 4.

When the term "alignment" or any of its variations are used herein with regard to a piercing member and a reconstitution port, it is intended to refer to a situation wherein selected structures of both overlap or come into communication or contact with each other. For example, the openings defined by the window 52 of the reconstitution port 36 and the interior aperture 66 of the piercing member 58 are exemplary structures that may be moved in and out of alignment, preferably to allow fluid and/or medicant to pass through both. In the illustrated embodiment of FIGS. 1-5, if there is no overlap between the openings and fluid flow is prevented, then it can be said that the window 52 and interior aperture 66 are "misaligned" or "not aligned" or some variation of those terms. When the interior aperture 66 and window 52 are aligned with each other, the flow path through the lumen 64 is open and fluid and/or medicant may be transferred into and out of the container 13 through the reconstitution port 36.

In a preferred embodiment, there is a visual or tactile indicator on the piercing member 58 which indicates that the lumen 64 is closed or open. For example, the piercing member 58 may be colored differently from the chamber 40, such that a user seeing the colored piercing member 58 through the clear plastic of the container wall and through the lateral window 52 will know that the window 52 and interior aperture 66 are misaligned and the reconstitution port 36 is closed.

Preferably, the piercing member 58 also includes at least one vial engagement member, illustrated as side spike 70 on or adjacent to the piercing spike 60. As shown in FIG. 5, the side spike 70 is configured such that it pierces into the pierceable membrane 46 of a medicant container 48 without passing entirely through the pierceable thickness t. When the side spike 70 engages the membrane 46, the piercing member 58 and container 48 are rotationally locked together, thereby allowing the piercing member 58 to be rotated by turning the attached container 48. It will be seen that the alignment of the window 52 and the interior aperture 66, and hence fluid communication between the attached medicant container 48 and the unitary container 13, is controlled by rotating the medicant container 48, which in turn rotates the spike. Although the docking sleeve 38 preferably prevents removal of an attached vial for tracing purposes, it allows relative rotational movement of an attached vial so that the user can selectively rotate the vial and therefore rotate the spike and spike aperture 66 into and out of communication with the window 52.

Most preferably, the present invention is used in combination with a vial 48 having a pierceable rubber stopper or septum 46 and containing a vial medicant M in an interior reservoir. The vial medicant M can be a medicant fluid or a solid, dehydrated composition. In order to make a treatment fluid comprising the combination of the bag fluid F and the vial medicant M, spike protector 68 is removed from the spike 60 and the stopper 46 of vial 48 is advanced into engagement with the docking sleeve 38 until the stopper 46 abuts the upper wall 42 and is locked into reconstitution port 36 by the slots 44. The vial 48 can be attached to the reconstitution port 36 with the container 13 being right-side up, as in FIG. 1, or in the inverted position, as in FIG. 4.

During insertion, spike 60 of piercing member 58 pierces through the pierceable thickness t of the stopper 46, placing the exterior aperture 62 in direct communication with the interior of the vial 48. However, as per a delayed activation aspect of the present invention, there is no immediate fluid communication between the bag fluid F and the vial medicant M due to the presence of the frangible member 54 within the window 52. Further, the lumen 64 may be auxiliary sealed at the interior aperture 66-lateral window 52 interface if they are not aligned. This allows the user to attach the vial but delay mixing and administration of the medicament until desired.

In an alternate embodiment (not shown). The vial engagement member may contain at least one additional pair of slots 44 or other suitable retention means to hold a vial in a initial lower position whereby the spike has not pierced the septum. Thus the container or vial 48 may be engaged to the port structure 14 prior to being provided to a customer and with the shelf life of the container 10 and vial not being impacted by the engagement of the vial to the container. Then at the appropriate time force may be applied to the vial to advance it into the higher set of slots 44 whereby the spike 60 penetrates the septum of the vial as described above.

Referring back to the preferred embodiment, in order to begin the mixing process, the frangible member 54 is removed from the window 52 and, if necessary, the interior aperture 66 and window 52 are aligned. This opens the lumen 64 to the flow of fluid F downwardly into the vial 48 by gravity, thereby mixing with the vial medicant M. The flow rate of fluid F may be controlled by controlling the amount of overlap between the window 52 and aperture 66. After the medicament or drug in the vial is reconstituted, and before administering the combined treatment fluid, the container 13 and vial 48 are inverted, as shown in FIG. 4, which evacuates all of the reconstituted medicament from the vial 48 by gravity. When the vial 48 is empty, it is rotated thereby causing rotation of the piercing member 58 until the interior aperture 66 moves away from the window 52 and the lumen 64 is resealed. Finally, the container 13 and vial 48 are reoriented right-side up, an administration set (not illustrated) is connected to the administration port 34, and the combined treatment fluid is delivered to a patient. Because the lumen 64 is sealed, no fluid from the container 13 flows into the vial 48 even though the vial is lower than the container.

The administration port 34 is configured to receive a standard administration set, for delivery of the treatment fluid to a patient. Preferably, the administration port 34 is temporarily sealed by a twist-off cap 72, which may be molded as one piece with the port structure, according to the design sold by Baxter International Inc. under the Viaflo™ trademark.

As illustrated, the reconstitution port 36 of FIG. 1 is preferably disposed at an angle to a vertical axis V of the container 13. Incidentally, it will also be seen that the reconstitution port 36 is at an angle to a horizontal axis H of the container 13. The angled configuration is useful for larger, wider vials because it reduces the risk of the vial interfering with the administration port 34. Further, in adapting the port structure 14 to accommodate an outwardly angled reconstitution port 36, section 74 of the bottom wall of the port structure 14 slopes downwardly from the reconstitution port 36 to the administration port 34, which serves to funnel the treatment fluid into the administration port 34 for improved delivery of the entire contents of the chamber 32.

Another aspect of the present invention which is useful, particularly with larger vials, is the use of a hanger aperture 24 which is laterally offset from a central vertical axis V of the container 13 and has multiple hanger locations. The seal at the top edge 16 of the container 13 is preferably reinforced or otherwise strengthened in order to provide additional support when the container 13 is hung from the hanger aperture 24. The aperture 24 is offset to the same lateral side of the top end 16 of the bag 12 as the reconstitution port 36 on the port structure 14, thereby compensating for the added weight of the attached vial and allowing for the container 13 to hang substantially vertically from a hanger (not illustrated). In a preferred embodiment, the hanger aperture 24 is laterally elongated and includes a plurality of notches 76 which are capable of accepting a hanger in different locations, depending on the size and weight of the attached vial. Of course, the reconstitution port 36 could be laterally centered itself, which would eliminate the risk of angled hanging, but that tends to aggravate the potential problem of interference between an attached vial and the administration port 34.

Figure 6:
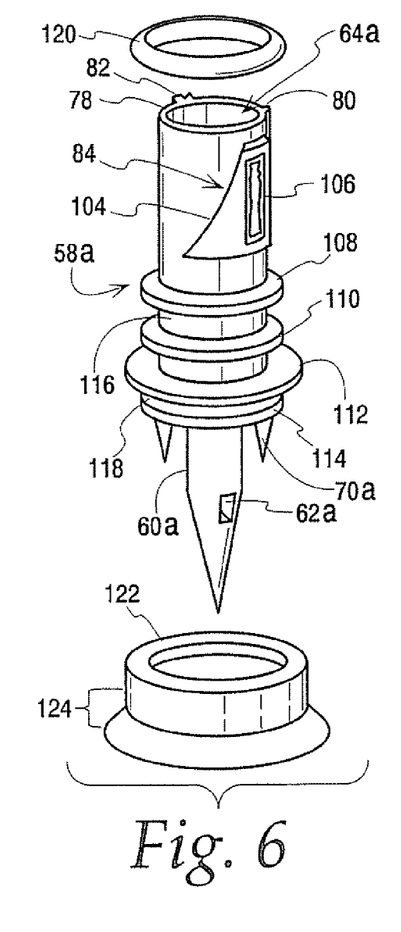
FIG. 6 is an exploded view of a piercing member according to another aspect of the present invention.

According to another aspect of the present invention, illustrated in FIGS. 6-11, a modified piercing member, reconstitution port, and port structure are provided. Elements thereof which are identified in FIGS. 6-11 by reference numbers appended with the suffix "a" correspond generally to the structures of FIGS. 1-5 without the suffix, and function substantially identically thereto unless otherwise noted. For example, FIG. 6 shows a piercing member 58a which is a variation on the previously described piercing member 58 of FIGS. 1-5.

The illustrated piercing member 58a has a hollow, generally tubular or cylindrical body with an inner lumen 64a extending between a top opening 78 at an upper or proximal end and a spike 60a at a lower or distal end. The spike 60a is sufficiently sharp to pierce through a pierceable membrane 46 of a medicant container 48 and preferably includes at least one vial engagement member or side spike 70a. The spike 60a further includes at least one exterior aperture 62a at a location which will pass into the interior of a medicant container 48 when the pierceable membrane 46 is pierced by the spike 60a. The illustrated spike 60a is generally tubular and narrower than the spike 60 of FIGS. 1-5, but it will be understood that either spike 60 or 60a may be used with a piercing member according to the present invention. Of course, it will be appreciated by those of skill in the art that other spike configurations that are not illustrated herein may also be acceptable.

Figure 8:
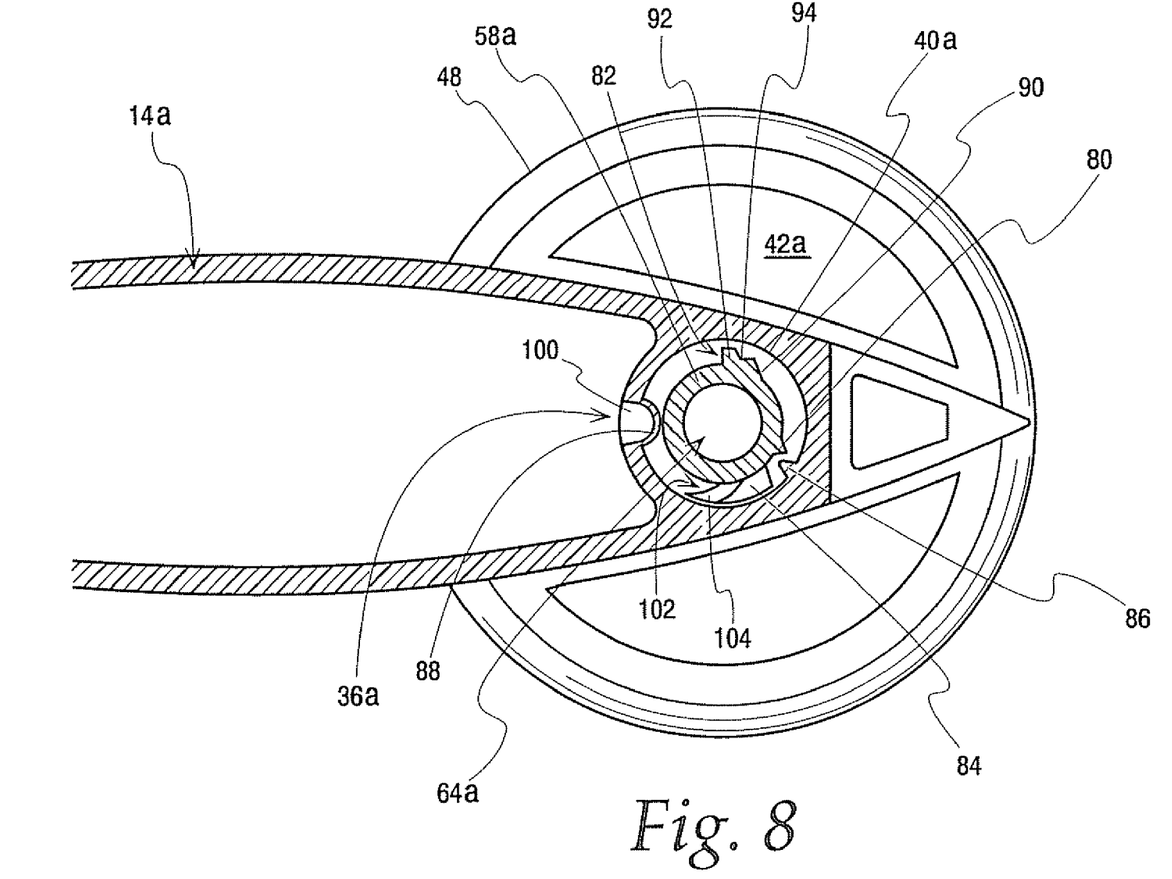
FIG. 8 is a top cross-sectional view of the piercing member of FIG. 6 in an initial position within the port structure of FIG. 7.
Figure 10:
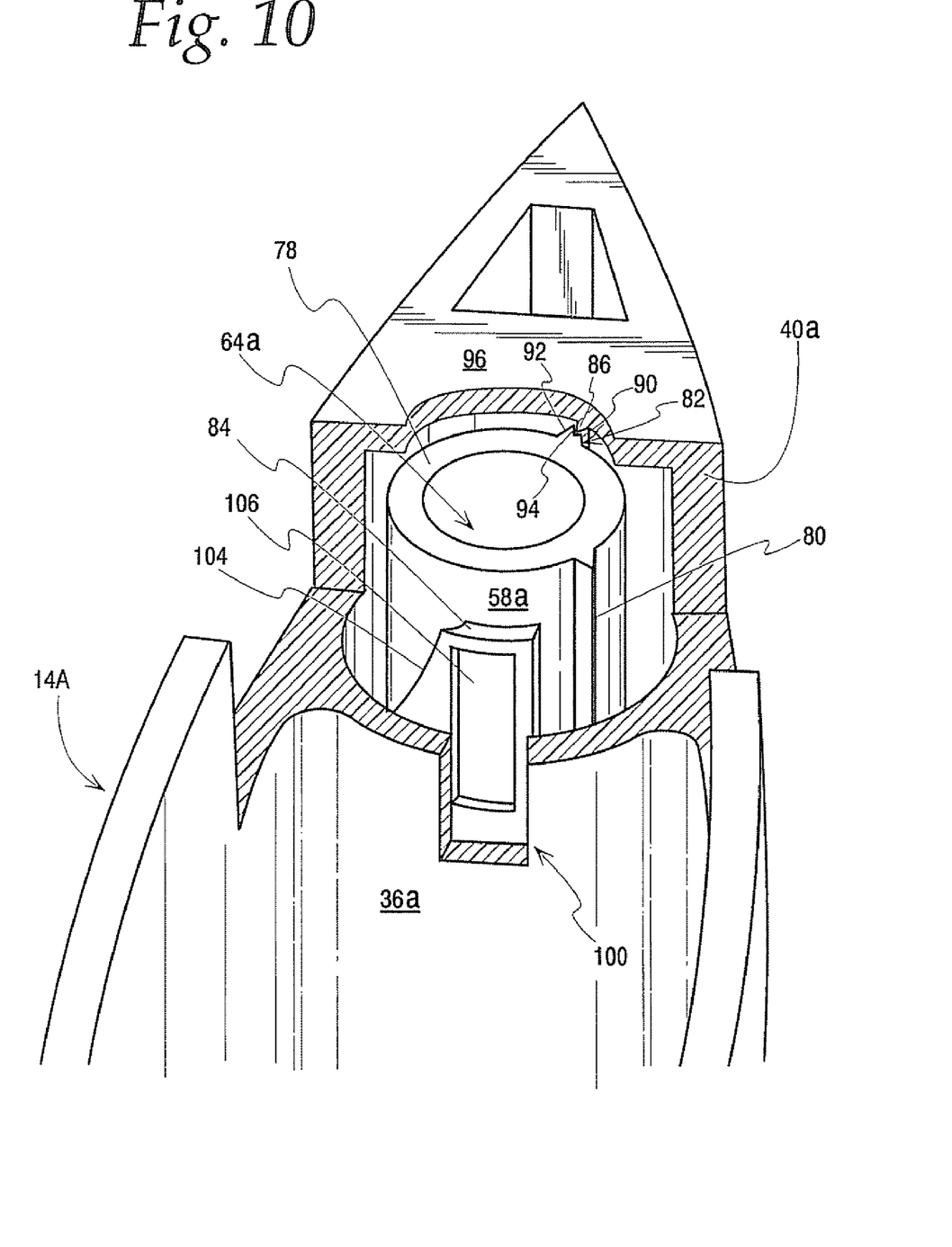
FIG. 10 is a side perspective view of the assembly of FIG. 8 in a final position, with certain parts broken away for clarity.

The outer surface of the piercing member 58a includes a leading projection 80, a trailing projection 82, and a cutter 84. The leading and trailing projections 80 and 82 are radially outwardly extending ridges or ribs that are adapted to interact with a radially inwardly extending inner barrier 86 of the reconstitution port 36a, which is shown in FIGS. 8 and 10. The piercing member 58a is rotatable within an inlet chamber 40a of the reconstitution port 36a between the initial position of FIG. 8 and the final position of FIG. 10. The leading and trailing projections 80 and 82 define the rotational limits of the piercing member 58a and act as tactile indicators for indicating whether fluid flow between the bag 12 and the piercing member 58a is open or closed.

In particular, the piercing member 58a is initially oriented in the inlet chamber 40a such that the inner barrier 86 is located between the cutter 84 and the leading projection 80. This initial position is shown in FIG. 8. The leading projection 80 projects to such an extent that it interferes with the inner barrier 86 when the piercing member 58a is rotated clockwise. When used herein, "clockwise" and "counterclockwise" can best be understood with reference to the configuration of FIG. 8. As will be described in greater detail herein, excess clockwise rotation of the piercing member 58a will allow fluid flow between the bag 12 and the piercing member 58a, so the interference between the leading projection 80 and the inner barrier 86 prevents accidental overrotation. Of course, the orientation of the components may be arranged such that the described rotation is reversed and the leading projection 80 resists counterclockwise rotation of the piercing member 58a.

As shown in FIG. 8, the leading projection 80 does not extend all of the way to the wall of the inlet chamber 40a, but projects to such an extent that the interference between the leading projection 80 and the inner barrier 86 can be overcome by persistent clockwise rotation of the piercing member 58a. An operator will be able to feel the leading projection 80 passing beyond the inner barrier 86, which serves as a tactile indicator that the piercing member 58a may be rotated clockwise without further resistance. The tactile indication may be accompanied by an audible signal, e.g., a "clicking" noise, as an additional indication that the leading projection 80 has passed beyond the inner barrier 86.

When the leading projection 80 has passed beyond the inner barrier 86, the piercing member 58a may be further rotated clockwise until the cutter 84 contacts a frangible member 88 of the reconstitution port 36a. This contact, when completed, allows fluid communication between the bag 12 and the piercing member 58a, as will be described below.

After the cutter 84 contacts the frangible member 88, further clockwise rotation of the piercing member 58a will eventually bring the trailing projection 82 into contact with the inner barrier 86. As best illustrated in FIG. 8, the trailing projection 82 preferably includes a minor ridge 90, of smaller radial extent than major ridge 92, which define a notch 94 therebetween. The minor ridge 90 is located clockwise of the major ridge 92, such that it comes into contact with the inner barrier 86 before the major ridge 92. Similar to the leading projection 80, the minor ridge 90 extends away from the piercing member 58a to such a degree that it may be rotated beyond the inner barrier 86 after some resistance. An operator will be able to feel the minor ridge 90 passing beyond the inner barrier 86, which serves as a tactile indicator that the piercing member 58a has reached the final position of FIG. 10 and that fluid communication between the bag 12 and the reconstitution port 36a is fully open. As with the leading projection 80, this tactile indication may be provided with an audible indication that further clockwise rotation is prevented.

When the inner barrier 86 has passed beyond the minor ridge 90, it will settle into the notch 94, as shown in FIG. 10. The major ridge 92 prevents further clockwise rotation of the piercing member 58a, while the minor ridge 90 provides resistance to counterclockwise rotation. Thus, the interaction between the trailing projection 82 and the inner barrier 86 allows the piercing member 58a to remain in the "open" position of FIG. 10, which allows fluid F in the bag 12 to mix with a medicant M in the container 48, as will be described below.

After mixing, the piercing member 58a may be rotated counterclockwise to the position of FIG. 8 to close fluid communication. The interaction between the inner barrier 86 and the leading projection 80 again provides a tactile indication, which indicates that fluid communication is closed. As illustrated in FIG. 8, the cutter 84 preferably extends away from the piercing member 58a until it is generally adjacent to the wall of the inlet chamber 40a. Thus, it will be appreciated that the cutter 84 limits counterclockwise rotation of the piercing member 58a by interfering with the inner barrier 86.

Proper operation of the above rotation system depends in part on maintaining the piercing member 58a in coaxial alignment with the inlet chamber 40a. Accordingly, as illustrated in FIG. 9A, the reconstitution chamber 36a preferably includes a top wall 96 with a closed nipple 98 that extends into the top opening 78 of the piercing member 58a. The closed nipple 98 may provide a relatively tight fit within the top opening 78 in order to prevent fluid leakage and to assist in properly orienting the piercing member 58a within the reconstitution port 36a while allowing rotation of the piercing member.

Figure 7:
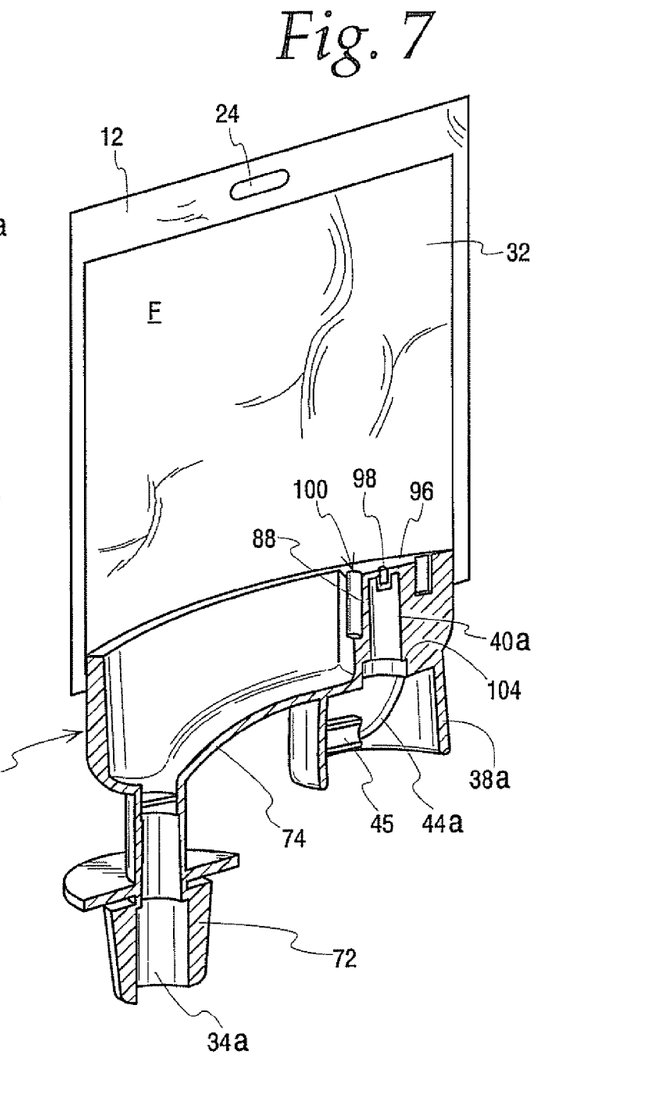
FIG. 7 is a perspective view of a cross section of a port structure for cooperation with the piercing member of FIG. 6 according to another aspect of the present invention.

Turning now to the opening action of the cutter, as shown in FIGS. 7 and 8, the reconstitution port 36a is initially sealed from the interior chamber 32 of the bag 12 to prevent fluid leakage. To provide for fluid communication between the chamber 32 and the lumen of the piercing member, the reconstitution port 36a is provided with a cut-away zone or access zone 100, which is an area between the interior chamber 32 and the inlet chamber 40a that is initially sealed by a frangible member 88. The frangible member 88 is at least partially cuttable and located such that contact with the cutter 84 will cause the frangible member 88 to at least partially separate from or open the access zone 100, creating an opening. In order to facilitate cutting, the frangible member 88 may be relatively thin. For example, FIG. 8 shows that the frangible member 88 is thinner than the adjacent walls of the reconstitution port 36a and the other walls of the port structure 14a. The exact configuration of the frangible member 88 is not critical, provided that it prevents fluid flow through the access zone 100 and extends into the rotational path of the cutter 84. However, the half-pipe configuration of FIGS. 7-10 is preferred for its interaction with a niche 102 associated with the cutter 84, as will be described herein.

In an alternate embodiment two cutters 84 may be provided and oriented such that rotation of the components may be in either a clockwise or a counterclockwise direction to bring one of the cutters into operational engagement with the frangible member 88. In such an embodiment, the piercing member 58a and the reconstitution port 36a may be fashioned with a plurality of leading projections 80, trailing projections 82, and inner barriers 86 arranged to provide tactile feedback and resistance according to the foregoing description upon rotation of the piercing member 58a in either direction.

Figure 11:
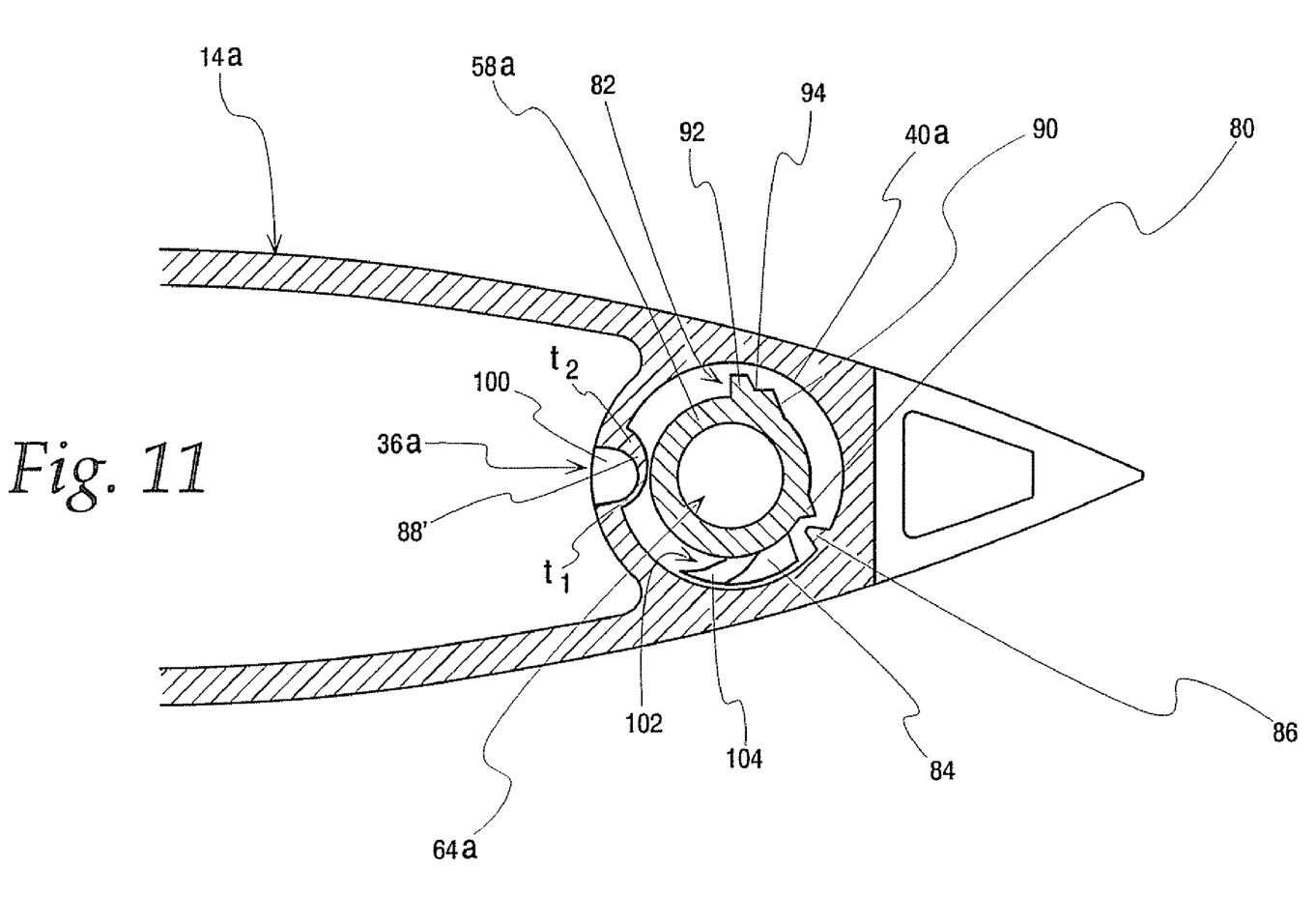
FIG. 11 is a top cross-sectional view of a port structure with a frangible member according to an alternative embodiment.

According to an alternative embodiment shown in FIG. 11, the reconstitution port 36a may be provided with a frangible member 88' having a varying thickness. In the illustrated embodiment, the frangible member 88' has a thickness which is tapered from a relatively thin portion $t_1$ to a thicker portion $t_2$. As will be seen, the frangible member 88' is thinner where it is first to be engaged and to be cut by the cutter 84 and thicker where it is to be retained by the reconstitution port 36a to reduce the risk of particulate generation. Those of skill in the art will appreciate that other variable-thickness frangible members are possible, and the illustrated embodiment is merely exemplary.

Turning back to the piercing member 58a, a preferred embodiment of which is illustrated in FIG. 6, an upper portion thereof includes a cutter 84. The cutter 84 has a sharpened, preferably angled cutting edge 104 and an interior aperture or cutter opening 106 which opens into the inner lumen 64a. Preferably, the cutting edge 104 is comprised of a material having a greater strength than the material used to form the port structure 14a and the frangible member 88. For example, in a preferred embodiment, the port structure 14a and the frangible member 88 are substantially comprised of an intermediate rigidity material, while the cutting edge 104 and the piercing member 58a are substantially comprised of a less flexible material. In an example the port structure may be formed of a high density polyethylene and the cutting edge 104 is formed of a polycarbonate.

Preferably, as illustrated in FIG. 8, the cutting edge 104 and the cutter 84 extend radially outward from the piercing member 58a such that they are adjacent to the wall of the inlet chamber 40a. It will be appreciated that the interaction between the wall of the inlet chamber 40a and the cutter 84 is sufficient to temporarily cover and seal the cutter opening 106. The illustrated cutting edge 104 is radially spaced from the piercing member 58a to define a curved, open niche 102 between the underside of the cutter 84 and the surface of the piercing member.

The outer surface of the piercing member 58a preferably includes a plurality of protruding annular ridges 108, 110, 112, and 114, which define channels 116 and 118 therebetween, located axially between the spike 60a and the cutter 84. The upper channel 116 is sized and configured to receive a first sealing member 120, illustrated in FIG. 6 as an o-ring, while the lower channel 118 is sized and configured to receive a second sealing member 122, illustrated as a b-shaped gasket. The first sealing member 120 contacts the inlet chamber 40a to prevent any fluid leakage into the environment after fluid flow has been established between the bag 12 and the piercing member 58a. The second sealing member 122 has a downwardly extending, preferably outwardly flared, skirt portion 124 which extends into the docking sleeve 38a and compresses against the stopper 46 of a medicant container 48 inserted into the reconstitution port 36a. The second sealing member 122 forms a seal with the stopper 46 to prevent fluid leakage into the environment and also acts as a cushion or spring when the medicant container 48 is pressed into the reconstitution port 36a to hold it tightly within the docking sleeve 38a.

Figure 9B:
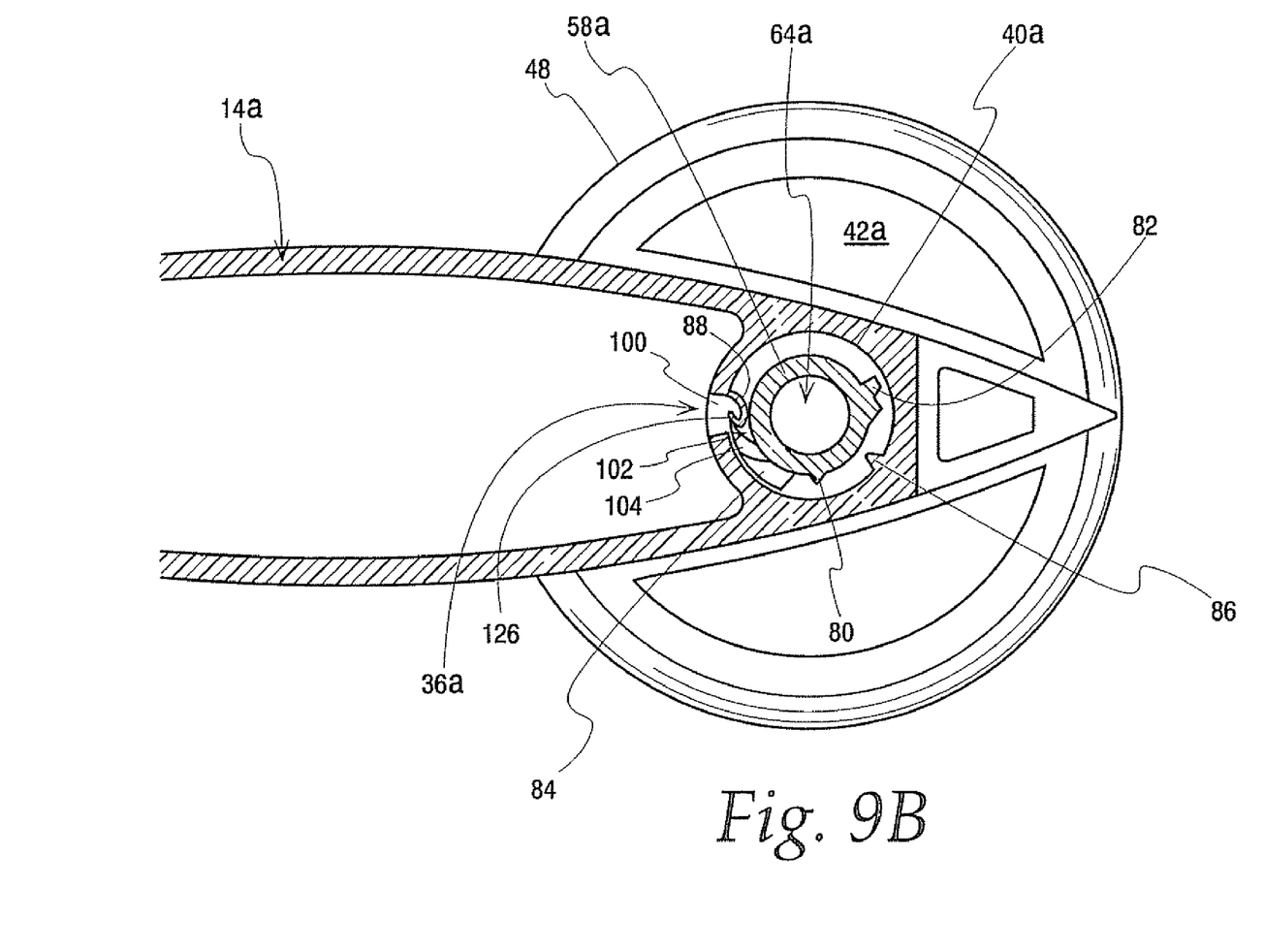
FIG. 9B is a top cross-sectional view of the intermediate position of FIG. 9A.

In use, the pierceable membrane 46 of a medicant container 48 is inserted into the reconstitution port 36a until it is engaged by the spike 60a and, if provided, the vial engagement members 70a. This initial position is shown in FIG. 8. Then, the medicant container 48 and the piercing member 58a are rotated clockwise until the leading projection 80 overcomes its interference with the inner barrier 86. Thereafter, the piercing member 58a is further rotated clockwise until the cutting edge 104 contacts and severs the frangible member 88, as illustrated in FIGS. 9A and 9B. In this position, the access zone 100 is partially open, but there is no flow between the bag 12 and the medicant container 48 because the cutter opening 106 is misaligned with the access zone 100. The sealing members 120 and/or 122 trap any incidental fluid leakage from the bag 12 through the access zone 100 within the inlet chamber 40a.

The piercing member 58a is further rotated to more fully sever the frangible member 88, open the access zone 100, and align the cutter opening 106 with the access zone 100, as shown in FIG. 10. As described previously, the trailing projection 82 prevents rotation of the piercing member 58a beyond the final position of FIG. 10. When the cutter opening 106 and the access zone 100 are in alignment with one another, a flow path between the interior chamber 32 of the bag 12 and the medicant container 48 is defined by the access zone 100, the cutter opening 106, the lumen 64a, and the exterior aperture 62a, by which the contents of the bag 12 and the medicant container 48 can be mixed.

After the medicant container 48 has been emptied into the bag 12, rotating the piercing member 58a counterclockwise to return it to the orientation of FIG. 8 may reseal the flow path therebetween. Finally, an administration set (not illustrated) may be connected to the administration port 34a, and the combined treatment fluid is delivered to a patient or other destination, such as an intermediate container or tubing flow set.

In a preferred embodiment, the frangible member 88 is partially cut away and moved from the access zone 100 by the cutting edge 104, but is not entirely separated from the reconstitution port. This is preferred, because a wholly separated frangible member could migrate into the administration port 34a and interfere with delivery of the treatment fluid. One way of achieving partial separation of the frangible member 88 is to provide a cutting edge 104 with a niche 102 and a relatively thin frangible member 88 with an arcuate configuration. In the position illustrated in FIGS. 9A and 9B, the cutting edge 104 has pierced through the frangible member 88 and a separated portion 126 of the frangible member 88 begins to curl behind the cutting edge 104, in the niche 102. As the piercing member 58a is further rotated to the position of FIG. 10, the separated portion 126 of the frangible member 88 continues to curl behind the cutting edge 104 and occupy the niche 102. In addition to being curved, the cutting edge 104 is also angled or inclined, such that at least an upper portion of the frangible member 88 remains uncut and attached to the reconstitution port 36a in the final position of FIG. 10.

In a further alternate embodiment, the piercing member 58a may be made of separate parts, wherein the spike 60a is a downward extension of the top wall 96 and the cutter 84 and other portions of the piercing member 58a are received within the inlet chamber 40a to rotate about the stationary spike 60a. In use, the upper end of a vial 48 is inserted into the reconstitution port 36a. The spike 60a extends through the stopper 46 and the engagement members 70a extend into the stopper 46. Rotation of the associated container 48 rotates the engagement members 70a and the cutting edge 104 until the cutting edge 104 severs the frangible member 88, 88' in a process similar to that described above. The spike 60a, however, remains stationary during the rotation. Fluid F then flows through the cutter opening 106, through the exterior aperture 62a of the stationary spike 60a, and into the container 48 for reconstitution. Although described with reference to the embodiment of FIGS. 6-11, a piercing member or assembly fashioned with a separate stationary spike according to the foregoing description may be equally applied to the embodiment illustrated in FIGS. 1-5.

Those skilled in the art will appreciate that numerous aspects of the embodiment of FIGS. 6-11 may be modified without departing from the scope of the present invention. For example, the use of a port structure 14a is not necessary and the administration and reconstitution ports 34a and 36a may be separate structures. Also, the positioning of the cutter 84 and the frangible member 88 may be reversed, with the cutter being a stationary component of the reconstitution port 36a and the frangible member being movable into contact with the cutter. The variations of the embodiment of FIGS. 1-5, such as an angled reconstitution port and a laterally offset hanger aperture 24, may also be practiced with the embodiment of FIGS. 6-11.

It will be understood that the embodiments of the present invention which have been described are illustrative of some of the applications of the principles of the present invention. Numerous modifications may be made by those skilled in the art without departing from the true spirit and scope of the invention, including those combinations of features that are individually disclosed or claimed herein. For example, the piercing member may be movable by other than rotation to control alignment of the fluid flow apertures. Also, alignment may occur by alignment of flow path portions in the piercing member and inlet chamber instead of direct alignment of the fluid flow apertures as employed in the illustrated embodiments. For these reasons, the scope of the invention is not limited to the above description but is as set forth in the following claims.

The invention claimed is:

1. A medicant reconstitution system comprising:
   a generally flexible bag defining an interior chamber capable of containing a medical fluid, and including a top end and a bottom end, wherein said bottom end includes an administration port for delivering a medical fluid to a patient;
   a reconstitution port associated with the bag and adapted to receive a medicant container having a pierceable membrane; and
   a piercing member rotatably received within said reconstitution port, wherein one of said reconstitution port and said piercing member includes a cutting edge and the other one of said reconstitution port and said piercing member includes a frangible member which is removable to define an opening therethrough, and wherein said piercing member is rotatable relative to the reconstitution port to bring said cutting edge and said frangible member into contact to open said frangible member.

2. The medicant reconstitution system of claim 1, wherein said cutting edge contacts said frangible member to allow fluid communication between said interior chamber and a medicant container received by said reconstitution port.

3. The medicant reconstitution system of claim 2, further comprising a visual, tactile, or audible indicator for indicating that fluid communication between said interior chamber and said medicant container is closed or open.

4. The medicant reconstitution system of claim 1, wherein said administration and reconstitution ports are integrally formed as part of a relatively rigid port structure.

5. The medicant reconstitution system of claim 4, wherein said port structure defines substantially the entire bottom end of said interior chamber.

6. The medicant reconstitution system of claim 1, wherein said reconstitution port is disposed at an angle to a vertical axis of said bag.

7. The medicant reconstitution system of claim 1, further comprising an engagement member associated with said piercing member and adapted to engage a medicant container in a rotationally fixed relationship, such that rotation of an engaged medicant container rotates said piercing member.

8. The medicant reconstitution system of claim 1, further comprising a hanger aperture adapted to receive a hook for suspending said bag, and wherein said hanger aperture and said reconstitution port are laterally offset to the same side of a central vertical axis of said bag.

9. The medicant reconstitution system of claim 1, wherein said frangible member has a varying thickness.

10. The medicant reconstitution system of claim 1, wherein said cutting edge is carried by said piercing member and radially spaced therefrom to define a cutting member to cut said frangible member.

11. The medicant reconstitution system of claim 1, wherein said reconstitution port is located at the bottom end of said generally flexible bag.

12. The medicant reconstitution system of claim 1, said one of the reconstitution port and said piercing member including a plurality of cutting edges, said piercing member rotatable in both clockwise and counterclockwise directions to open said frangible member.

13. The medicant reconstitution system of claim 1, said piercing member further including a spike configured to pierce said generally flexible bag.

14. The medicant reconstitution system of claim 13, said piercing member further including at least one side spike.

15. The medicant reconstitution system of claim 1, at least one of said cutting edge and said frangible member configured such that said frangible member when cut is not completely removed from said piercing member or the reconstitution port.

16. The medicant reconstitution system of claim 1, which includes at least one sealing member positioned between said piercing member and said reconstitution port.

17. The medicant reconstitution system of claim 1, said piercing member rotatable in a first direction to open said frangible member and rotatable in a second direction to seal medical fluid between said reconstitution port and said piercing member.

18. The medicant reconstitution system of claim 1, wherein said cutting edge is made of a less flexible material than said frangible member.

* * * * *